(12) United States Patent
Smith et al.

(10) Patent No.: US 8,544,481 B1
(45) Date of Patent: Oct. 1, 2013

(54) BRUSH AND TOSS (76) Inventors: Gloria Smith, College Park, GA (US);
Alanna Smith-Dorsey, College Park, GA (US)

( * ) Notice: Subject to any disclaimer, the term of this patent is extended or adjusted under 35 U.S.C. 154(b) by 0 days.

(21) Appl. No.: 13/526,339

(22) Filed: Jun. 18, 2012

Related U.S. Application Data (60) Provisional application No. 61/507,765, filed on Jul. 14, 2011.

(51) Int. Cl.
| *A45D 44/18* | (2006.01) |
| *A46B 11/00* | (2006.01) |
| *A46B 15/00* | (2006.01) |
| *A46B 11/04* | (2006.01) |
| *A47L 13/22* | (2006.01) |
| *B43K 29/00* | (2006.01) |

(52) U.S. Cl.
USPC ............ 132/309; 132/311; 401/195; 401/270

(58) Field of Classification Search
USPC ................. 132/308–311, 200, 317, 318, 320, 132/321, 323–329; 206/277, 581, 823, 368; 206/209; 15/167.1; 401/145, 184, 185, 195, 401/270, 271, 284, 287, 286, 289
See application file for complete search history.

(56) References Cited

U.S. PATENT DOCUMENTS

| 1,711,183 | A | * | 4/1929 | Smith ............................. 401/175 |
| 2,113,439 | A | * | 4/1938 | Bean ............................. 132/309 |
| 3,738,762 | A | * | 6/1973 | Moore et al. .................. 401/186 |
| 3,782,397 | A | * | 1/1974 | McCord ........................ 132/309 |
| 3,861,406 | A | * | 1/1975 | Stitt .............................. 132/309 |
| 4,176,980 | A | * | 12/1979 | O'Neal et al. ................ 401/162 |
| 4,530,129 | A | * | 7/1985 | Labick et al. .................. 15/184 |
| 4,583,563 | A | | 4/1986 | Turner |
| 4,865,481 | A | * | 9/1989 | Scales ........................... 401/195 |
| 4,950,095 | A | * | 8/1990 | Picard .......................... 401/191 |
| 4,987,910 | A | * | 1/1991 | Lowe ............................ 132/309 |
| 5,097,852 | A | * | 3/1992 | Wu ............................... 132/309 |
| 5,348,028 | A | * | 9/1994 | Gustavel ...................... 132/309 |
| 5,439,014 | A | | 8/1995 | Moussa |
| 5,490,530 | A | * | 2/1996 | Snowden ..................... 132/311 |
| 5,599,126 | A | * | 2/1997 | Hough ......................... 401/184 |
| 5,676,167 | A | * | 10/1997 | Garner ......................... 132/309 |
| 5,769,553 | A | * | 6/1998 | Chaudhri et al. ............ 401/195 |
| 5,865,195 | A | * | 2/1999 | Carter .......................... 132/309 |
| 5,881,425 | A | * | 3/1999 | Hudson et al. ............... 15/167.1 |
| 5,908,257 | A | | 6/1999 | Martin |
| 5,924,429 | A | * | 7/1999 | Morando ..................... 132/309 |
| 5,950,641 | A | * | 9/1999 | Taveras ....................... 132/309 |
| 6,142,694 | A | | 11/2000 | Rivlin et al. |

(Continued)

*Primary Examiner* — Vanitha Elgart (74) *Attorney, Agent, or Firm* — R G Patent Consulting LLC; Rachel Gilboy (57) ABSTRACT

A disposable tooth care system including: a toothbrush and floss assembly having a toothbrush having a proximate end and a distal end; a handle; a pouch located in the inner volume, the pouch is flexible and contains toothpaste; a floss spool comprising a wound-length of dental floss; and an axle. The handle includes; an outer surface; an inner volume; and a forked end; a neck; a head with at least one dispensing aperture; bristles; and a button. The toothbrush and floss assembly comprises the toothbrush; the pouch located in the inner volume of the handle of the toothbrush; the floss spool carried by the axle rotatable in the forked end, the axle fixed to the handle within the forked end, the forked end located at the proximate end of the toothbrush.

9 Claims, 5 Drawing Sheets

(56) References Cited

U.S. PATENT DOCUMENTS

| | | |
|---|---|---|
| 6,257,791 B1 | 7/2001 | Scamard |
| 6,851,882 B1 * | 2/2005 | Maloney .................. 401/183 |
| 7,201,172 B2 * | 4/2007 | Nanda ..................... 132/309 |
| 7,234,473 B1 * | 6/2007 | Winters ................... 132/309 |
| 7,237,560 B2 * | 7/2007 | Macias et al. ............ 132/309 |
| 8,015,982 B2 * | 9/2011 | Wilkinson ............... 132/309 |
| 8,201,688 B2 * | 6/2012 | Burfiend et al. .......... 206/361 |
| 2002/0114658 A1 | 8/2002 | Allen et al. |
| 2003/0086745 A1 * | 5/2003 | Micaletti et al. ......... 401/179 |
| 2003/0150472 A1 * | 8/2003 | Johnson .................. 132/311 |
| 2003/0188761 A1 * | 10/2003 | Garcia et al. ............ 132/309 |
| 2005/0211262 A1 * | 9/2005 | Raab ....................... 132/309 |
| 2009/0188519 A1 * | 7/2009 | VanBuskirk et al. .... 132/309 |
| 2013/0000658 A1 * | 1/2013 | Nguyen et al. ........... 132/200 |

* cited by examiner

BRUSH AND TOSS

CROSS-REFERENCE TO RELATED APPLICATION

The present application is related to and claims priority from prior provisional application Ser. No. 61/507,765, filed Jul. 14, 2011 which application is incorporated herein by reference.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of tooth care devices and more specifically relates to a disposable tooth care system, entitled 'brush and toss systems'.

2. Description of the Related Art

A variety of oral hygiene measures have been used to protect teeth. Toothbrushes may be used as an oral hygiene instrument to clean the teeth and gums. Toothbrushes are typically comprised of a head of tightly clustered bristles mounted on a handle, which facilitates the cleansing of hard-to-reach areas of the mouth. Toothbrushes are available with different bristle textures, sizes and forms. Most dentists recommend using a toothbrush labeled "soft", since firmer bristled toothbrushes can damage tooth enamel and may irritate the gums. Toothbrushes have been made from synthetic fibers in recent years, although animal bristles may still be sometimes used.

Toothpaste is a paste or gel dentifrice used/applied with a toothbrush as a means to clean and maintain the aesthetics and health of teeth. Toothpaste is used to promote oral hygiene acting as an abrasive that aids in removing the dental plaque and food from the teeth, assists in the elimination and/or masking of halitosis, and delivers active ingredients such as fluoride or xylitol to help prevent tooth and gum disease(s) such as gingivitis. Toothpaste, which often contains fluoride, is commonly used in conjunction with a toothbrush to increase the effectiveness of teeth brushing.

Dental floss is made of either a bundle of thin nylon filaments or a plastic (Teflon® or polyethylene) or a silk ribbon used to remove food and dental plaque from teeth. The floss is gently inserted between the teeth and scraped along the teeth sides, especially close to the gums. Dental floss may be flavored or unflavored, and waxed or unwaxed. An alternative tool to achieve the same effect is the interdental brush. An alternative tool to achieve the same effect is the interdental brush. When spending extended periods of time away from home, consumers are required to have consistent access to dental hygiene products. However, packing several items such as toothbrushes, toothpaste, and dental floss can be highly inconvenient. The items may take up unnecessary space in luggage, and toothpaste may leak out and spill onto clothing or other items within the luggage. Also, individuals who are handicapped, who are experiencing declining agility, or who are very young and have underdeveloped motor skills may have significant difficulty squeezing traditional toothpaste tubes may have difficulty with conventional devices and systems.

Various attempts have been made to solve the above-mentioned problems such as those found in U.S. Pat. and Pub. Nos. 6,257,791; 5,908,257; 6,142,694; 5,439,014; 2002/0114658; and 4,583,563. This prior art is representative of tooth care means. None of the above inventions and patents, taken either singly or in combination, is seen to describe the invention as claimed.

Ideally, a disposable tooth care system should be convenient, user-friendly and, yet would operate reliably and be manufactured at a modest expense. Thus, a need exists for a reliable disposable tooth care system to avoid the above-mentioned problems.

BRIEF SUMMARY OF THE INVENTION

In view of the foregoing disadvantages inherent in the known tooth care art, the present invention provides a novel disposable tooth care system. The general purpose of the present invention, which will be described subsequently in greater detail, is to provide efficiency and convenience for individuals when caring for their teeth, especially when the individual is not at his/her residence.

The Brush & Toss provides consumers with several dental hygiene aids in one compact and disposable device; wherein the toothbrush, paste, and spool of floss comprises an all in one appliance. This innovative product preferably features a disposable toothbrush containing a toothpaste-dispensing pouch (the paste inside the toothbrush) and a roll of dental floss, which may be integrated. Users may press down on the pouch to dispense the toothpaste directly onto the bristles for instant use. The paste is emitted directly onto the bristled surface of the toothbrush via a canal/channel within the toothbrush and out through slits/ducts. The dispensing device is a sealed flexible bulb/button shaped device in the handle of the toothbrush situate above the inner pouch. A plastic or cellophane pouch holds the paste and is seated inside the volume of the toothbrush handle. The paste may be dispensed by putting pressure on the flexi bulb/button dispenser that in turn releases the paste from the pouch and onto the bristled surface. The floss is wound onto a spool and set in an axle in the heel of the toothbrush and is able to be rotated independently to dispense at the convenience of brusher user. Due to the self-contained construction of this invention, consumers may use it when traveling, camping, or staying in hospitals without having to pack several dental hygiene products. Additionally, the ease with which the toothpaste can be dispensed may allow elderly, handicapped, and very young individuals to independently and comfortably use this product.

A disposable tooth care system is disclosed herein, in a preferred embodiment, comprising: a toothbrush and floss assembly. The toothbrush and floss assembly includes a toothbrush having a proximate end and a distal end; a handle; a pouch located in the inner volume (the pouch is flexible and contains toothpaste); a floss spool comprising a wound-length of dental floss; and an axle. The handle includes; an outer surface; an inner volume; and a forked end; a neck; a head with at least one dispensing aperture; bristles; and a depressible button. The outer surface of the handle of the toothbrush comprises a hand-gripping surface whereby a brusher-user may manipulate the toothbrush. For safety reasons (in children's versions) the spool/axle may be fixed within the forked end of the heel and only the floss can be completely removed via the pull away plastic/cellophane tab.

The toothbrush and floss assembly is a self-contained-tooth-cleaning-system. The toothbrush and floss assembly comprises the toothbrush. The pouch is located substantially in the inner volume of the handle of the toothbrush. The floss spool carried by the axle is rotatable in the forked end, the axle fixed to the handle within the forked end, the forked end located at the proximate end of the toothbrush. The toothbrush and floss assembly is useful to provide the toothpaste and the dental floss to the brusher-user to clean the teeth of the brusher-user to promote oral hygiene. The floss spool when rotated about the axle is able to dispense a portion of the wound-length of dental floss when pulled by the brusher-user. The wound-length of dental floss comprises about twelve inches in preferred embodiments and a light adhesive may be used to attach the floss tab to the spool/axle. The floss is able to be pulled free of the spool and ready for use immediately or removed and taken for use as desired or left attached to brush for later use. Further the dental floss is isolated from germs in an ambient environment via a cellophane pull-off tab when not in use.

The neck is located between the handle and the head. The head supports the bristles; the bristles mounted perpendicularly to the head. The bristles are useful for brushing the teeth of the brusher-user. The head is located at the distal end of the toothbrush. The head preferably comprises exactly three dispensing apertures whereby the toothpaste may egress therefrom, however may be less or more in alternate embodiments.

The pouch comprises a collapsible plastic in preferred embodiments. The channel terminates with the dispensing apertures. The dispensing apertures are located perpendicular to the channel. The channel is located through the handle, through the neck and through the head such that the toothpaste in the pouch is in communication to supply the toothpaste via the channel to the bristles when the pouch is squeeze-manipulated via the brusher-user. A cellophane pouch containing the paste is seated inside the volume of the toothbrush handle. The dispensing apertures (3) are located within and parallel to the bristles. One above and two below (all facing in the direction of the bristles such that the toothpaste may be dispensed); the pouch comprises an internally mounted container/pouch is accessible via (or integral with) the flexi-button; the button when depressed causing the toothpaste to be dispensed through the channel and out the aperture (s). The channel terminates at the inner volume, the pouch open to inner volume such that the pouch when squeeze-manipulated is able to supply the toothpaste to the channel. The toothpaste travels through the channel to the at least one dispensing aperture to dispense at the bristles such that the toothpaste is accessible to the brusher-user. The toothbrush comprises an internally mounted tubular pouch that is located approximately 2 inches below the head of the toothbrush within the handle and fixed beneath the flexible dispensing aperture (preferably holds approximately ½ ounce of toothpaste or gel.) The small tubular shaped, cellophane pouch/container resides in a small reservoir of the toothbrush with a channel that leads into the neck of the brush where the toothpaste or jell may be emitted from the perforated end leading into the neck cavity. By putting pressure on the (seated and sealed) flexible, dispensing button located in the handle of the toothbrush (flexibility enhances the emission process) and when pressed forces the paste through the canal and out the apertures onto the bristled surface. (The cellophane pouch also keeps the paste fresh and sanitary.)

A method of use for a disposable tooth care system is also disclosed herein comprising the steps of: dispensing a volume of toothpaste out of a pouch located in an inner volume of a handle of a toothbrush through a channel and through dispensing apertures onto bristles; brushing teeth of a brusher-user; cleaning the bristles when completed; and rotating a floss spool to dispense a length of dental floss such that the brusher-user is able to floss between the teeth to promote oral hygiene. The step of dispensing may be enabled via a button.

The present invention holds significant improvements and serves as a disposable tooth care system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention, which are believed to be novel, are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, disposable tooth care (brush & toss) system, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a toothbrush and floss care device and more particularly to a disposable tooth care system as used to improve the convenience of brushing and flossing processes.

Generally speaking, 'Brush & Toss' (disposable tooth care system) is designed to present consumers with all necessary dental items in one convenient product. The invention may comprise a toothbrush made of disposable, recycled plastic or other environmentally-friendly materials. In the center of the handle can be a flexible, pressure-sensitive pouch containing toothpaste. A canal or channel may extend from the pouch, through the neck of the brush, to three holes integrated into the head of the brush. Users can simply press on the pouch (or button) to dispense the toothpaste, causing the toothpaste to be emitted through the holes and onto the bristles of the brush. At the bottom end of the invention may be a small spool, onto which a 12" line of dental floss may be wound. The floss can be protected by a plastic or cellophane pull-off tab, which may cover the floss while applied to the brush, and can be removed for easy access to the floss. This product may be available in a variety of sizes to accommodate the needs of children and adults, and can be made in a variety of colors to suit user preferences. This product can be used for children's sleepovers, camping trips, staying in hospitals, staying in hotels, and a wide array of other purposes.

Figure 1:
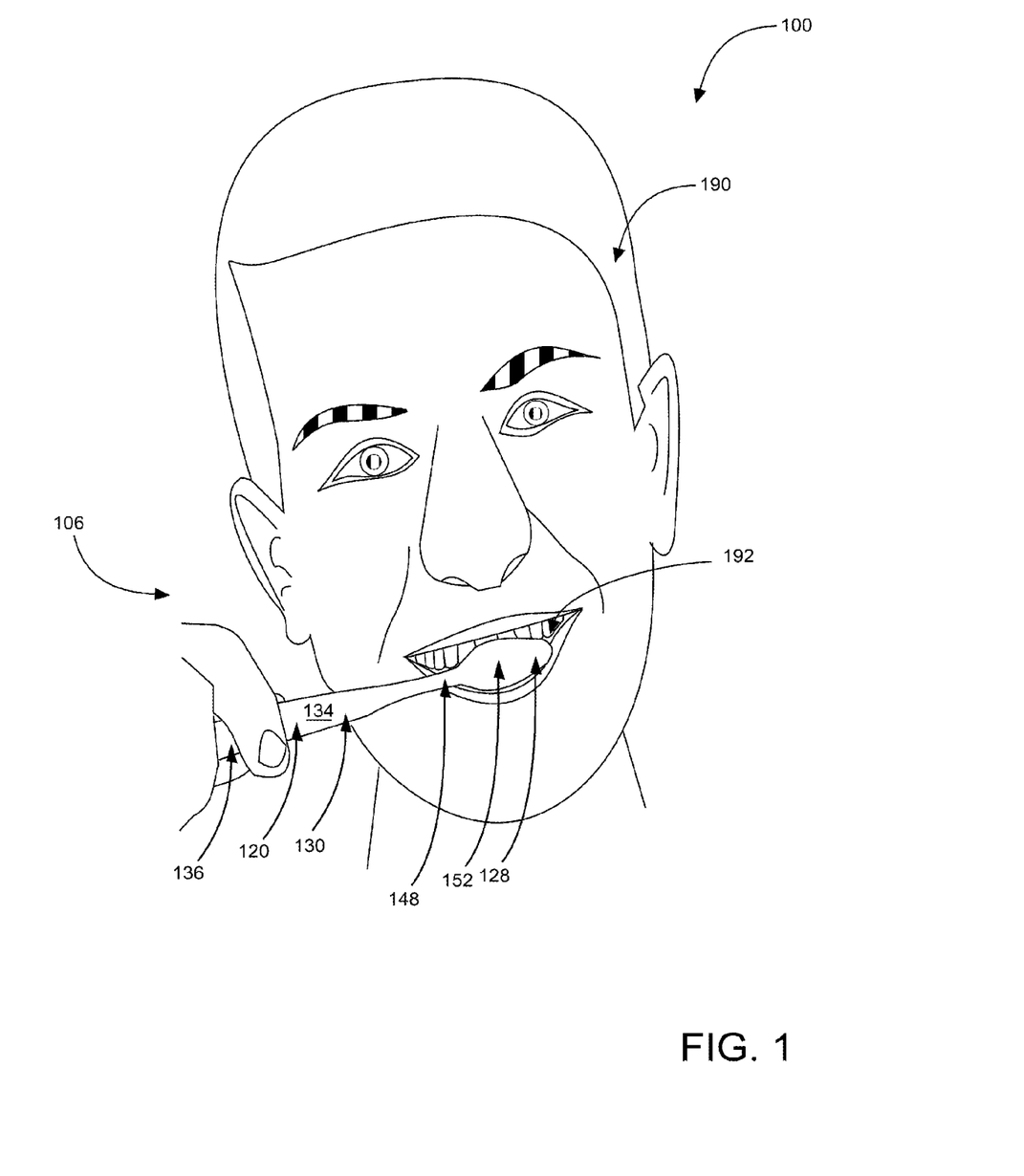
FIG. 1 shows a perspective view illustrating a disposable tooth care system in an in-use condition according to an embodiment of the present invention.

Referring to the drawings by numerals of reference there is shown in FIG. 1, a perspective view illustrating disposable tooth care system 100 in in-use condition 106 according to an embodiment of the present invention.

Disposable tooth care system 100 preferably comprises toothbrush and floss assembly 110. Toothbrush and floss assembly 110 includes toothbrush 120 having proximate end 124 and distal end 128. toothbrush 120 comprises handle 130 including outer surface 134, and inner volume 138; forked end 142; neck 148; head 152 with at least one dispensing aperture 156, and bristles 160; pouch 164 which is located in inner volume 138. Pouch 164 is flexible and contains toothpaste 168. Floss spool 172 comprises a wound-length of dental floss 176, and axle 180 for rotating thereon in relation to handle 130.

Toothbrush and floss assembly 110 comprises toothbrush 120, as previously mentioned. Toothbrush and floss assembly 110 is useful to provide toothpaste 168 and dental floss 176 to brusher-user 190 to clean teeth 192 of brusher-user 190 to promote oral hygiene. Pouch 164 is preferably located in inner volume 138 of handle 130 of toothbrush 120. Floss spool 172 carried by axle 180 is rotatable in forked end 142, axle 180 able to be normally fixed to handle 130 (within forked end 142); forked end 142 located at proximate end 124 of toothbrush 120. Floss spool 172 when rotated about axle 180 is able to dispense a portion of the wound-length of dental floss 176 when pulled by brusher-user 190.

Outer surface 134 of handle 130 of toothbrush 120 comprises hand-gripping surface 136 whereby brusher-user 190 may manipulate toothbrush 120. Head 152 supports bristles 160; bristles 160 mounted preferably substantially perpendicularly to head 152, bristles 160 useful for brushing teeth 192 of brusher-user 190. Neck 148 is located between handle 130 and head 152. Head 152 is located at distal end 128 of toothbrush 120.

Channel 132 is located through handle 130, through neck 148 and through head 152 such that toothpaste 168 in pouch 164 is in communication to supply toothpaste 168 via channel 132 to bristles 160 when pouch 164 is squeeze-manipulated via brusher-user 190. Toothpaste 168 travels through channel 132 to at least one dispensing aperture 156 to dispense at bristles 160 such that toothpaste 168 is accessible to brusher-user 190.

Figure 2:
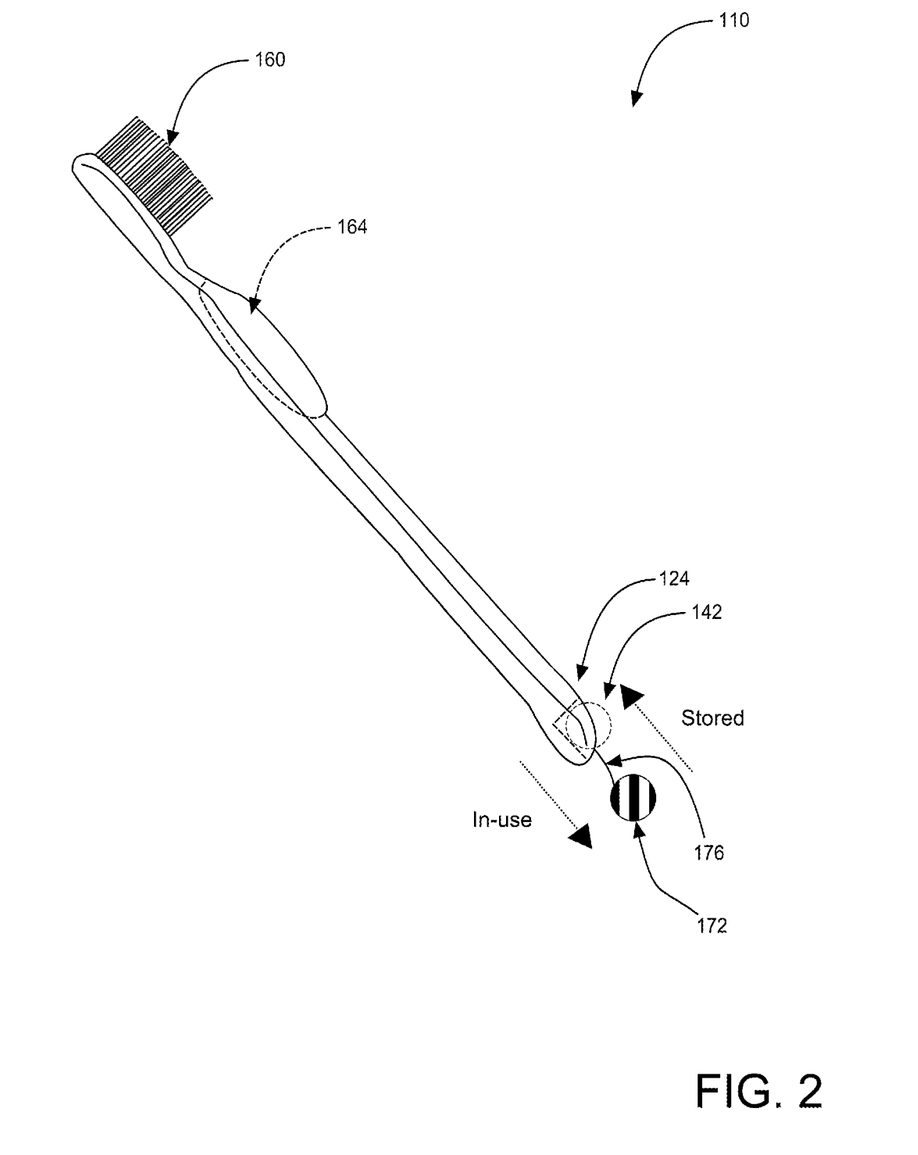
FIG. 2 is a side perspective view illustrating a toothbrush and floss assembly according to an embodiment of the present invention of FIG. 1.

Referring now to FIG. 2, showing a side perspective view illustrating toothbrush and floss assembly 110 according to an embodiment of the present invention of FIG. 1.

Toothbrush and floss assembly 110 is a self-contained-tooth-cleaning-system. Head 152 comprises exactly three dispensing apertures 156 whereby toothpaste 168 may egress therefrom. Toothbrush 120 comprises recycled plastic. Upon reading this specification, it should be appreciated that, under appropriate circumstances, considering such issues as user preferences, design preference, structural requirements, marketing preferences, cost, available materials, technological advances, etc., other material arrangements such as, for example, metal(s), non-metals, rubber, thermoplastics, non-thermoplastics, composites, etc., may be sufficient.

Toothbrush 120 preferably comprises a length of about 6 inches or greater in preferred embodiments, this particular embodiment of toothbrush 120 is useful by an adult brusher-user 190. Further, toothbrush 120 comprises a length of less than 6 inches in other embodiments, toothbrush 120 useful by a child brusher-user 190, given its smaller size. Other lengths may be used comprising shorter or longer versions as per the brushing needs of brusher-user 190.

Figure 3:
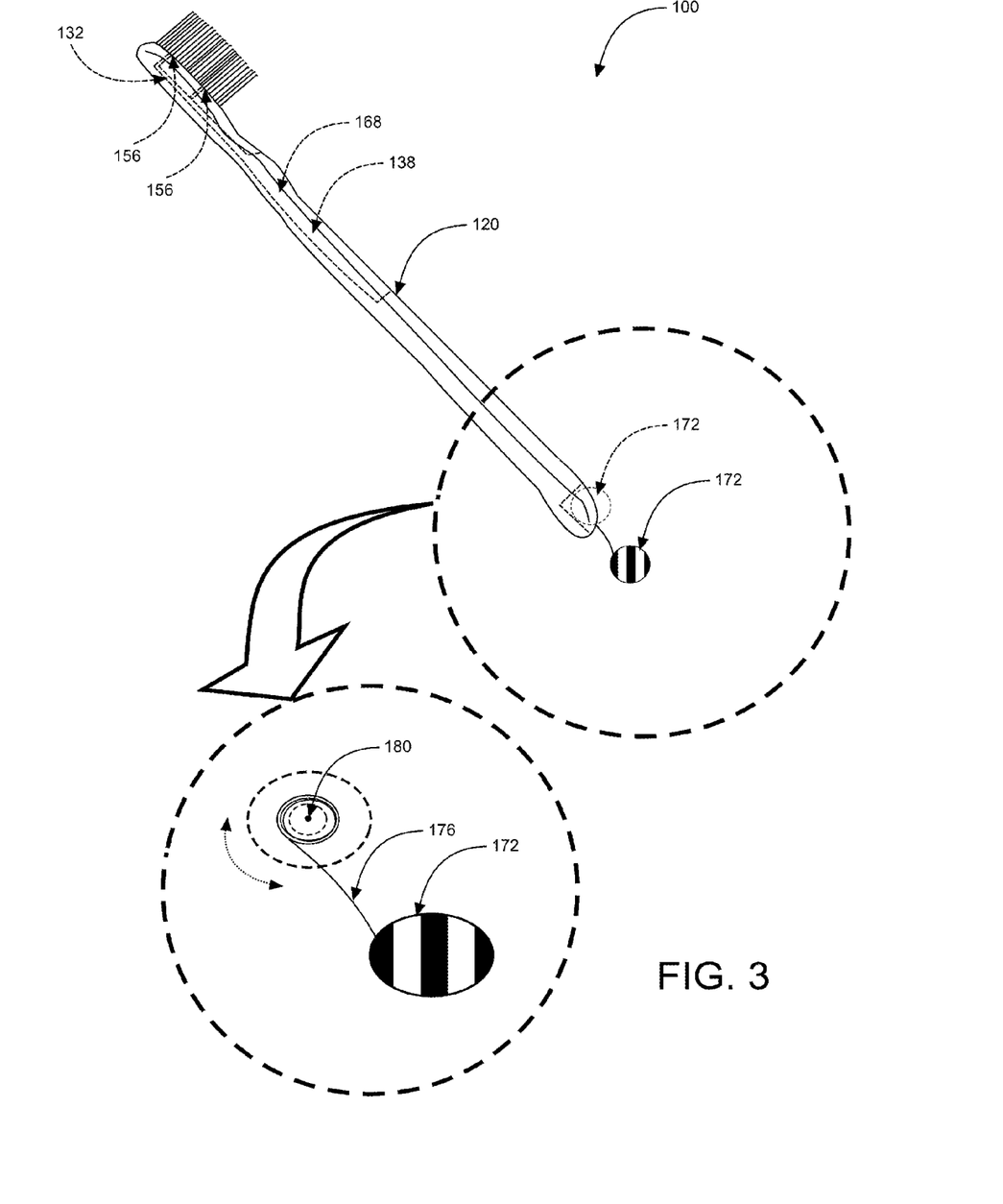
FIG. 3 is a side perspective view illustrating the toothbrush and floss assembly having a floss spool comprising a wound-length of dental floss according to an embodiment of the present invention of FIG. 1.

Referring now to FIG. 3, a side perspective view illustrating toothbrush and floss assembly 110 having floss spool 172 comprising a wound-length of dental floss 176 according to an embodiment of the present invention of FIG. 1.

Dental floss 176 may be isolated from germs in an ambient environment via cellophane pull-off tab 178. Wound-length of dental floss 176 comprises about twelve inches, however more or less dental floss 176 may be used as per a need of brusher-user 190. Floss spool 172 is removable from toothbrush and floss assembly 110 by removing axle 180. axle 180 may function in a similar capacity to watch pins having depressible telescopic sections. Floss spool 172 is able to be rewound with dental floss 176.

Figure 4:
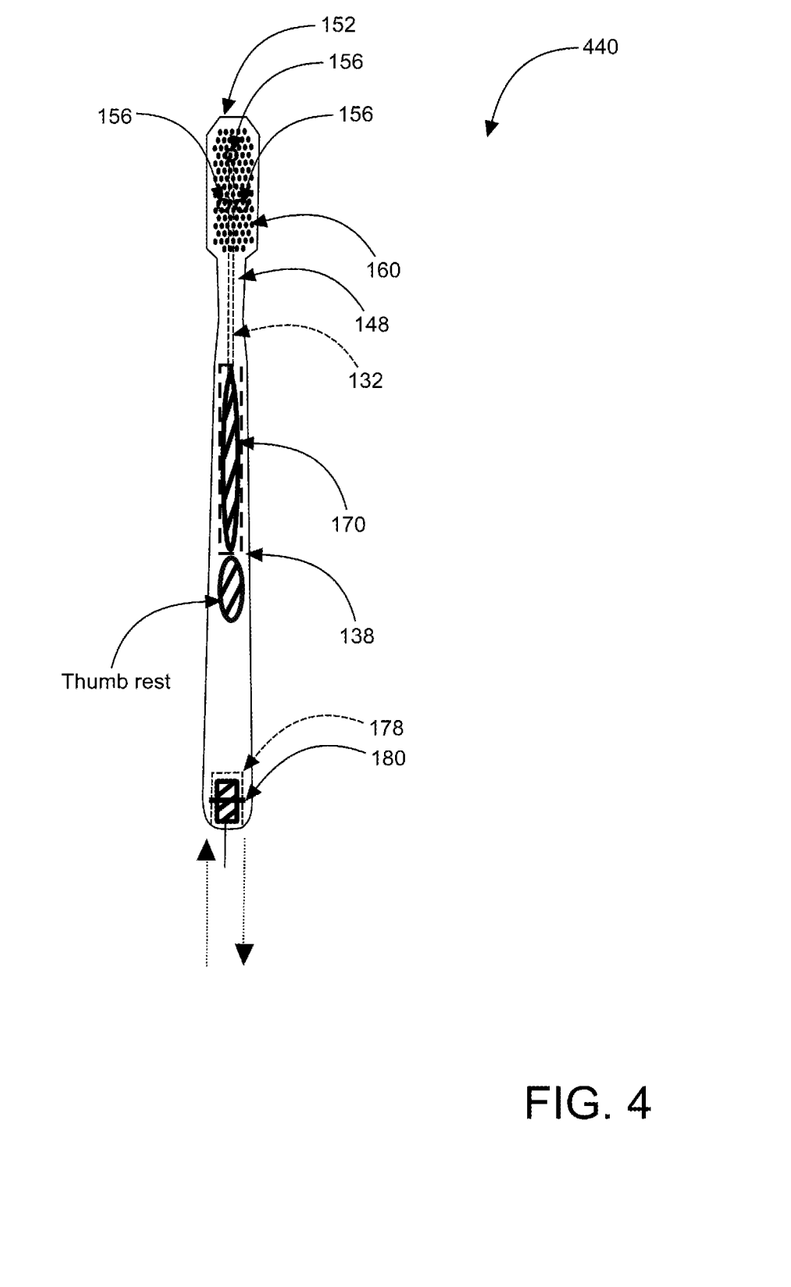
FIG. 4 is a top view illustrating the toothbrush and floss assembly according to an embodiment of the present invention of FIGS. 1-3.

Referring now to FIG. 4, top view illustrating toothbrush and floss assembly 110 according to an embodiment of the present invention of FIGS. 1-3.

Pouch 164 preferably comprises internally-mounted tubular container 166. Pouch 164 is preferably accessible via button 170; button 170 when depressed causing toothpaste 168 to be dispensed through channel 132 and out aperture(s) 156. Pouch 164 comprises a collapsible plastic. Upon reading this specification, it should be appreciated that, under appropriate circumstances, considering such issues as user preferences, design preference, structural requirements, marketing preferences, cost, available materials, technological advances, etc., other pouch materials such as, for example, aluminum-plastic laminated film, plastic and aluminum etc., may be sufficient.

Channel 132 preferably terminate with dispensing apertures 156. Channel 132 terminates at inner volume 138; pouch 164 open to inner volume 138 such that pouch 164 when pressed-manipulated is able to supply toothpaste 168 to channel 132. In certain embodiments two of dispensing apertures 156 are located at a rear of head 152 and another of dispensing apertures 156 located at a front of head 152, dispensing apertures 156 located within and (substantially) parallel to bristles 160, as shown. Dispensing apertures 156 are located (substantially) perpendicular to channel 132. When brusher-user 190 runs out of toothpaste 168, pouch 164 may be refilled with toothpaste 168 thereby preventing brusher-user from having to purchase a new disposable tooth care system 100 every time toothpaste 168 is depleted from pouch 164. In this way the present invention is cost-effective in use. Alternately, pouch 164 may simply be readily disposed of when out of toothpaste 168. The disposable tooth care system 100 is practical and cost effective by providing a safer more sanitary product that will lessen the opportunity to carry germs from one user to another and through the elimination of waste through the purchase individual tooth care supplies for short trips and sleepovers, hospital stays, etc.

Disposable tooth care system 100 may be sold as kit 440 comprising the following parts: at least one toothbrush 120 having at least one refillable pouch 164 housing toothpaste 168; at least one replaceable floss spool 172 housing dental floss 176; and at least one set of user instructions. Disposable tooth care system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 5:
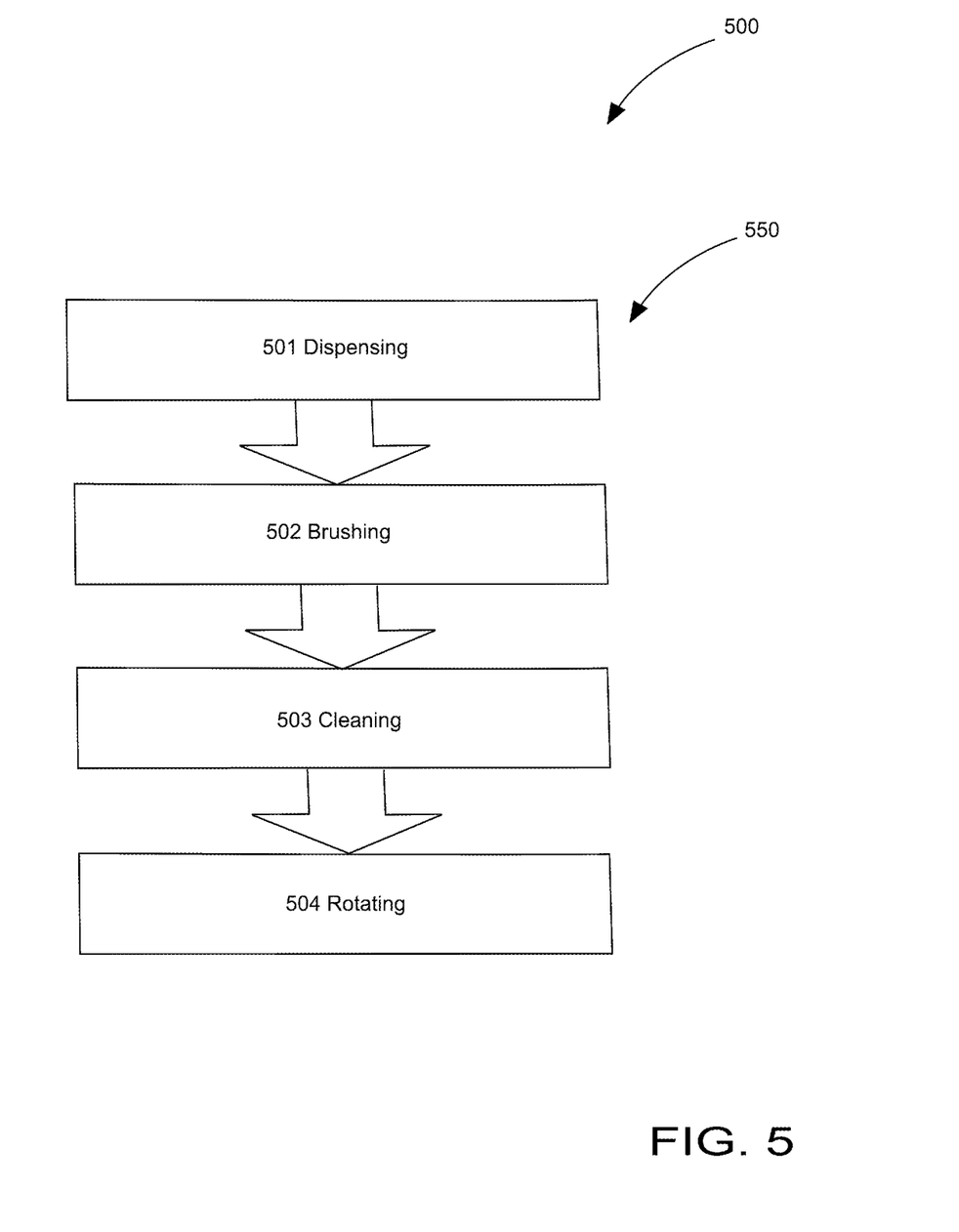
FIG. 5 is a flowchart illustrating a method of use for the disposable tooth care system according to an embodiment of the present invention of FIGS. 1-4.

Referring now to FIG. 5, a flowchart 550 illustrating a method of use 500 for disposable tooth care system 100 according to an embodiment of the present invention of FIGS. 1-4.

Method of use 500 for disposable tooth care system 100 comprises the steps of: step one 501 dispensing a volume of toothpaste 168 out of pouch 164 located in inner volume 138 of handle 130 of toothbrush 120 through channel 132 and through dispensing apertures 156 onto (through) bristles 160; step two 502 brushing teeth 192 of brusher-user 190; step three 503 cleaning bristles 160 when completed; and step four 504 rotating floss spool 172 to dispense a length of dental floss 176 such that brusher-user 190 is able to floss between teeth 192 to promote oral hygiene. The step of dispensing is enabled via use of button 170 or otherwise pressing/pushing upon button 170 (which may comprise a flexi-button.)

It should be noted that the steps described in the method of use could be carried out in many different orders according to user preference. The use of "step of" should not be interpreted as "step for", in the claims herein and is not intended to invoke the provisions of 35 U.S.C. §112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A disposable tooth care system comprising:
   a) a toothbrush and floss assembly including;
      i) a toothbrush having a proximate end and a distal end;
         (1) a handle including;
            (a) an outer surface;
            (b) an inner volume; and
            (c) a forked end;
         (2) a neck;
         (3) a head with at least one dispensing aperture;
         (4) bristles; and
         (5) a button;
      ii) a pouch located in said inner volume;
      iii) said pouch is flexible and contains toothpaste;
      iv) a floss spool comprising a wound-length of dental floss; and
      v) an axle;
   b) wherein said toothbrush and floss assembly is a self-contained-tooth-cleaning-system;
   c) wherein said toothbrush and floss assembly comprises said toothbrush;
   d) said pouch located in said inner volume of said handle of said toothbrush;
   e) said floss spool carried by said axle rotatable in said forked end, said axle removably fixed to said handle within said forked end, said forked end located at said proximate end of said toothbrush;
   f) wherein said toothbrush comprises recycled plastic;
   g) wherein said outer surface of said handle of said toothbrush comprises a hand-gripping surface whereby a brusher-user may manipulate said toothbrush;
   h) wherein said floss spool when rotated about said axle is able to dispense a portion of said wound-length of dental floss when pulled by said brusher-user;
   i) wherein said wound-length of dental floss comprises about twelve inches;
   j) wherein said dental floss is isolated from germs in an ambient environment via a cellophane pull-off tab when not in use;
   k) wherein said pouch comprises a flexible plastic;
   l) wherein said neck is located between said handle and said head;
   m) wherein said head supports said bristles, said bristles mounted perpendicularly to said head, said bristles useful for brushing teeth of said brusher-user;
   n) wherein said head is located at said distal end of said toothbrush;
   o) wherein said head comprises exactly three said dispensing apertures whereby said toothpaste may egress there from;
   p) wherein channel terminates with said dispensing apertures;
   q) wherein said dispensing apertures are located perpendicular to said channel;
   r) wherein said channel is located through said handle, through said neck and through said head such that said toothpaste in said pouch is in communication to supply said toothpaste via said channels to said bristles when said pouch is squeeze-manipulated via said brusher-user;
   s) wherein two of said dispensing apertures are located at a rear of said head and another of said dispensing apertures located at a front of said head, said dispensing apertures located within and parallel to said bristles;
   t) wherein said pouch comprises an internally-mounted container, said pouch accessible via integral said button, said button when depressed causing said toothpaste to be dispensed through said channel and out said aperture(s);
   u) wherein said channel terminates at said inner volume, said pouch opens to said inner volume such that said pouch when squeeze-manipulated is able to supply said toothpaste to said channel;
   v) wherein said toothpaste travels through said channel to said at least one dispensing aperture to dispense at said bristles such that said toothpaste is accessible to said brusher-user; and
   w) wherein said toothbrush and floss assembly is useful to provide said toothpaste and said dental floss to said brusher-user to clean said teeth of said brusher-user to promote oral hygiene.

2. A method of use for said disposable tooth care system of claim 1 comprising the steps of:

a) dispensing a volume of said toothpaste out of said pouch located in said inner volume of said handle of said toothbrush through said channel and through said dispensing apertures onto said bristles;
b) brushing teeth of said brusher-user;
c) cleaning said bristles when completed; and
d) rotating said floss spool to dispense a length of said dental floss such that said brusher-user is able to floss between said teeth to promote oral hygiene.

3. The method of claim 2 wherein said step of dispensing is enabled via said button.

4. The disposable tooth care system of claim 1 wherein said pouch comprises a collapsible plastic.

5. The disposable tooth care system of claim 1 wherein said floss spool is removable from said toothbrush and floss assembly by removing said axle.

6. The disposable tooth care system of claim 1 wherein said floss spool can be rewound with dental floss.

7. The disposable tooth care system of claim 1 wherein said pouch is refillable with toothpaste.

8. The disposable tooth care system of claim 1 wherein said toothbrush comprises a length of approximately 7 and ½ inches, said toothbrush useful by an adult said brusher-user.

9. The disposable tooth care system of claim 1 wherein said toothbrush comprises a length of approximately 6 inches, said toothbrush useful by a child said brusher-user.

* * * * *